US006934028B2

(12) United States Patent
Ho et al.

(10) Patent No.: US 6,934,028 B2
(45) Date of Patent: Aug. 23, 2005

(54) CERTIFICATION AND VERIFICATION MANAGEMENT SYSTEM AND METHOD FOR A WEB INSPECTION APPARATUS

(75) Inventors: Morris D. Ho, Petaluma, CA (US); Stuart R. Dole, Petaluma, CA (US); Warren Berkholtz, Petaluma, CA (US); Jason Berry, Petaluma, CA (US)

(73) Assignee: Webview, Inc., Santa Rosa, CA (US)

( * ) Notice: Subject to any disclaimer, the term of this patent is extended or adjusted under 35 U.S.C. 154(b) by 331 days.

(21) Appl. No.: 09/765,829

(22) Filed: Jan. 19, 2001

(65) Prior Publication Data

US 2001/0030749 A1 Oct. 18, 2001

Related U.S. Application Data

(60) Provisional application No. 60/177,246, filed on Jan. 20, 2000.

(51) Int. Cl.[7] .................. G01N 21/84; G01N 21/00; G01N 21/86; G06K 9/00; G01B 5/28
(52) U.S. Cl. .................. 356/430; 356/237.1; 382/141; 250/559.01; 702/35
(58) Field of Search ................ 356/429, 430, 356/237.1; 382/141; 250/559.01, 559.4; 702/35, 40, 81, 108, 182, 187, 188

(56) References Cited

U.S. PATENT DOCUMENTS

| | | | |
|---|---|---|---|
| 3,458,261 A | | 7/1969 | Bentley et al. |
| 3,551,678 A | | 12/1970 | Mitchell |
| 3,835,332 A | * | 9/1974 | Bridges .................. 250/559.04 |
| 3,843,890 A | | 10/1974 | Anthony et al. |
| 3,970,857 A | * | 7/1976 | Buckson .................. 250/559.1 |
| 4,166,541 A | * | 9/1979 | Smith, Jr. .................. 209/587 |
| 4,170,419 A | * | 10/1979 | Van Tyne et al. ............ 356/431 |
| 4,237,539 A | | 12/1980 | Piovoso et al. |
| 4,670,659 A | * | 6/1987 | Loose .................... 250/559.04 |
| 5,006,722 A | * | 4/1991 | Adelson ................. 250/559.47 |
| 5,068,799 A | * | 11/1991 | Jarrett, Jr. ..................... 702/40 |
| 5,365,596 A | * | 11/1994 | Dante et al. ................. 382/141 |
| 5,440,648 A | * | 8/1995 | Roberts et al. ............. 382/141 |
| 5,715,181 A | * | 2/1998 | Horst ......................... 702/180 |
| 5,774,177 A | * | 6/1998 | Lane ........................... 348/88 |
| 5,960,374 A | * | 9/1999 | Lausier ........................ 702/81 |
| 6,026,172 A | * | 2/2000 | Lewis et al. ................ 382/106 |
| 6,084,681 A | * | 7/2000 | Keane ........................ 356/430 |
| 6,236,429 B1 | * | 5/2001 | Ho ............................... 348/88 |
| 6,266,436 B1 | * | 7/2001 | Bett et al. .................... 382/141 |

FOREIGN PATENT DOCUMENTS

| | | |
|---|---|---|
| EP | 0477536 A2 | 4/1992 |
| JP | 09229909 | 9/1997 |
| JP | 2000146859 | 5/2000 |

* cited by examiner

Primary Examiner—Zandra V Smith
Assistant Examiner—Gordon J. Stock, Jr.
(74) Attorney, Agent, or Firm—Beyer Weaver & Thomas LLP

(57) ABSTRACT

A certification system and method for inspecting of a roll of web material through a web inspection system which includes the inspection of the roll of web material to determine the number, type and location of one or more detectable flaws along the web material. This data "object" representation of the roll map is recorded, and then compared to predetermined product set-up parameters and machine vision hardware integrity data to determine the accuracy of the web inspection. The generated "certification" assures with a substantial degree of precision that the machine vision hardware is calibrated and operating correctly, and that the correct system setup parameters for the particular web product being inspected are being applied.

60 Claims, 11 Drawing Sheets

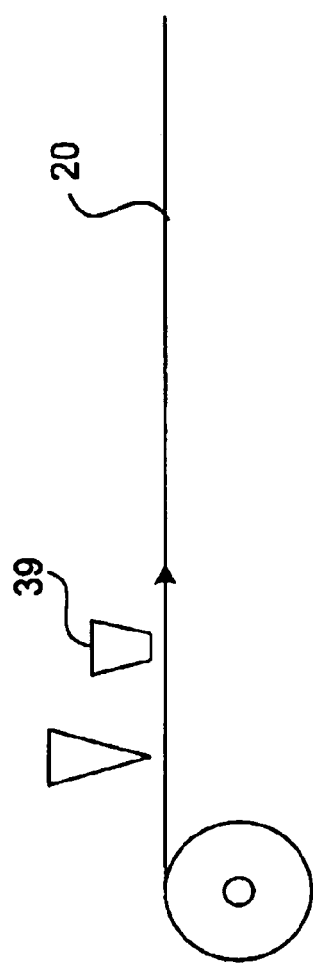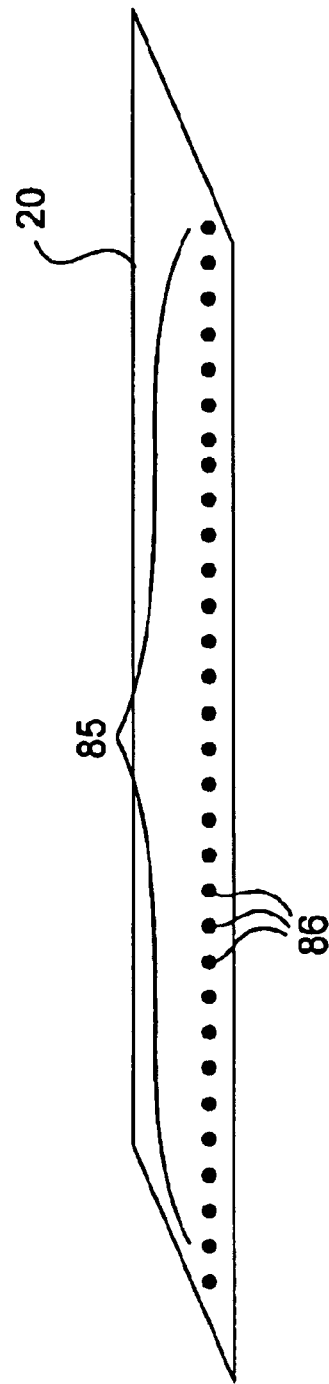

Shipper Windup

Receiver Unwind

CERTIFICATION AND VERIFICATION MANAGEMENT SYSTEM AND METHOD FOR A WEB INSPECTION APPARATUS

CROSS REFERENCE TO RELATED APPLICATIONS

This application claims priority of U.S. patent provisional application No. 60/177,246, filed Jan. 20, 2000, which is incorporated herein by reference in its entirety for all purposes.

TECHNICAL FIELD

The present invention relates, generally, to web inspection assemblies and, more particularly, relates to systems and methods for certifying and verifying the inspection results for high speed, high resolution web inspection assemblies.

BACKGROUND ART

As technology advances, the quality control of particular web (sheet and roll) products become increasingly important. These web products may be required to be completely free of certain kinds of flaws ("catastrophic" flaws), or to not exceed a certain number of flaws per unit area. Even though these may be specified in the product specifications, and in the purchaser's contract, there are no simple ways to certify or verify the actual quality of the web product.

One example of a type of catastrophic flaws are lithium-ion battery membrane flaws which can cause a watch battery to fail explosively. Other examples of catastrophic flaws in web products include bio-tech filter failure which allow bacteria into medications that could be fatal to a patient with a suppressed immune system, or a radiologist with one look at an x-ray film with a coating defect will never use that brand of film again.

Consequently, in recent years, considerable effort has been directed toward visual web inspection to enhance the uniform quality of material webs, such as these battery membranes and filter materials, as well as paper, glass, plastic, textiles, metallic sheets, fiberglass and sheet substrates. These web inspection systems are capable of high speed, high-resolution detection and classification of surface imperfections in continuously manufactured products at rates in excess of 500 inches per second. Such surface imperfections include tears, through-holes, abrasions and scattering imperfections, impurities preventing local processing, stains and absorbing imperfections, pinch marks, thickness imperfections, and other far side and near side imperfections.

Briefly, web inspection assemblies often include; an illumination source generating a point of light or a strip of light, and a photoelectric light sensor device or a conventional linear Charge Coupled Device (CCD) array or camera strategically positioned and angled to receive diffusely reflected light from a target surface illuminated by the generated light. Due to the scattering imperfections on or in the target surface, differences in light intensity of the reflected or transmitted light will be detected which may represent one of the above-mentioned surface imperfections. The light sensor device then delivers a signal to an electronic processing device representative of the type and magnitude of the surface imperfection.

These current web inspection systems, however, are limited in several respects. For instance, the current automated web inspection systems require hundreds of variables (inspection parameters) that need to be precisely set to enable a proper inspection. However, these settings may be unintentionally (or intentionally!) modified, which skews flaw detection and reporting. Moreover, these systems use proprietary software file structures that thwart verification of setup parameters, calibration, and open diagnostic monitoring of the inspection system.

Other problems associated with these current inspection systems is that they use proprietary Graphic User Interfaces (GUIs) that require anyone accessing the system to be physically present at the system's computer on the factory floor. Further, these proprietary inspection system file structures do not have the open architecture that enables easy tracking and verification of the hundreds of parameters necessary to verify and certify flaw detection reporting adequately to certify production to purchase orders corresponding to a specific web roll or web products.

Moreover, the current web inspection assemblies do not allow for secondary inspection or the web. When electronic Roll Maps of the web roll are recorded during prior inspections of the web material, the web surfaces are often not properly synchronized to effectively and precisely outline the flaw types and their locations. The specific location of the flaw, and the flaw type, cannot be accurately determined and classified along the web roll. This is particularly detrimental when the web products require a series of downstream applications at the same or different manufacturing systems. In this situation, even if the type of flaws and their locations are determined, the accuracy of such information deteriorates quickly.

As a result, the presence of a few detected flaws, affecting only a tiny fraction of the total material, will cause an entire lot (i. e., web roll) to be rejected. This is primarily due to the fact that although the flaws have been detected, their exact locations along the web are not accurately known, if they are known at all. Thus, separation or removal of the defective material from the remaining web portions cannot be precisely performed. Consequently, vast quantities of these good quality materials are unnecessarily discarded.

The quality control sought, therefore, is difficult to quantify, verify, and guarantee, even with expensive and labor-intensive initiatives to synchronize inspection results to existing process databases. These defect-critical products are manufactured and sold with little more than promises and good intentions of quality, certification of fitness for use, and compliance with purchase orders.

Accordingly, an apparatus and method of web inspection is needed which enables certification and verification of the actual quality of the web product.

DISCLOSURE OF INVENTION

In accordance with the foregoing, a method is provided for inspection of a roll of web material through a web inspection system. The method includes inspecting the roll of web material to determine the number, type and location of one or more detectable flaws along the web material, and outputting a data "object" representation of the roll map. The method further includes certifying the accuracy of the roll map object representation of the inspected web material to be within a predetermined range of tolerances.

Accordingly, the generated "certification" assures with a substantial degree of accuracy that the machine vision hardware (i.e., the web inspection system) is calibrated and operating correctly. This signifies that a self-diagnosis has been performed successfully within a specified time, and the signals from the cameras are consistent with correct operation. The "Product Inspection Certificate" further assures that the correct system setup parameters for the particular web product being inspected are being used. The customer's engineering staff typically sets up these parameters to achieve the desired level of defect detection, on a product-by-product basis. The Product Inspection Certificate specifies which set of parameters were used, and that they have not been altered. Finally, another main objective of the Product Inspection Certificate is to assure that the flaw report and roll map are what the system generated, and not a fabrication.

In one embodiment, before the certifying, the method include performing a self-diagnostic test on the inspection system to determine the performance of the web inspection by the inspection system. This includes measuring or retrieving certification data applied during the inspection; and comparing the applied certification data to standardized certification data to determine whether the applied certification data was within the predetermined range of tolerances.

Another embodiment includes a System Integrity Test measuring performance and calibration of predetermined components of the web inspection system, and performing a Product Calibration Test measuring the application of product set-up parameters for the particular web material inspected.

The certification data includes System Integrity Test Data relating to the calibration and operation of predetermined components of the web inspection system, and Product Calibration Test Data reviewing the product set-up parameters applied for the particular web material inspected.

In another aspect, the present invention includes a web inspection certification system to certify an inspection a roll of web material through a web inspection system. The certification system includes a web inspection system adapted to inspect the roll of web material to detect at least one or more flaws, if any, in the web material. Further, a diagnostic device is adapted to measure or retrieve the actual certification data of the web inspection system applied or to be applied during said web inspection corresponding to the particular web material being inspected. Finally, a certifying device is adapted to certify the accuracy of the data "object" representation of a roll map of the inspected web material when the applied certification data conforms, within a predetermined tolerance, to standardized certification data for the roll of web material.

In one embodiment of this configuration, a location analysis device is adapted to determine the location of the at least one detected flaw, relative the roll of web material, through fiduciary indicators placed along the web material. Further a recording device records the detection of the at least one detected flaw, and its location relative the roll of web material create the data "object" representation of a roll map thereof.

In one embodiment, the diagnostic device performs a Self-Diagnostic Test which measures the System Integrity Test Data of predetermined components of the web inspection system to assure proper calibration and operation thereof. Such predetermined components include the vision hardware of the web inspection system including the cameras, the lenses, and light sources. The actual certification data, in addition to the System Integrity Test Data, further includes Product Calibration Data corresponding to the particular web material being inspected to certify what inspection set-up parameters were employed during the web inspection, and that they have not been altered.

A time stamp device may be included in one configuration to time stamp the occurrence of the diagnostic by the diagnostic device. This information, together with actual certification data, the predetermined certification data, and the roll map data may be included in a certification report.

In still another embodiment, a defect analysis device is included which determines the cause of the detected defects. This is primarily performed by comparing the measured defect data of the at least one detected defect with existing defect data of a process-control database. The measured defect data and the vision process data are stored in Relational databases enabling SQL access to the post inspection results. Consequently, this format enables simple data sharing and export with third-party tools.

The fiduciary indicators may be included by spaced-apart fiduciary marks placed along the roll of web material. These fiduciary marks may be spaced-apart along an edge of the web material, or they may be markings on the non-inspected side of the web, should one exist. In other embodiments, the fiduciary indicators are the actual detected one or more defects relative to their placement along the roll of web material.

In another aspect of the present invention, a method is provided for certifying an inspection of a roll of web material through a web inspection system. The method includes calibrating the web inspection system to conform to predetermined certification data for the roll of web material to be inspected, and inspecting the roll of a web material for one or more defects, if any, through the web inspection system. The method further includes detecting at least one of the one or more defects through the web inspection system, and determining the location of the at least one detected defect, relative the roll of web material, through fiduciary indicators placed along the web material. The next step includes recording the detection of the at least one detected defect, and its location relative the roll of web material on a recording medium to create a roll map. To effect certification, the method includes measuring the actual certification data of the web inspection system, and comparing the actual certification data to the predetermined certification data for the roll of web material. Finally, the method includes certifying the accuracy of the roll map of the inspected web material when the actual certification data is within a predetermined tolerance of the predetermined certification data.

In one embodiment, the measuring of the actual certification data of the web inspection system includes performing a Self-Diagnostic Test on the predetermined components to generate the actual certification data. This self-diagnostic test is triggered manually, periodically within a predetermined time interval, or automatically with each web inspection run. The measuring further includes determining what inspection parameters were employed during the web inspection, and that they have not been altered.

In another embodiment, the method further includes determining the cause of the at least one detected defect. This is provided by comparing the measured defect data of the at least one detected defect with existing defect data of a process-control database.

Yet another embodiment includes re-inspecting the roll of web material through the same web inspection system or an independent second web inspection system to verify the certification by detecting the at least one of the one or more defects through the web inspection system;

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 9A is a diagrammatic side elevation view of a roll of web material with a fiduciary marker device marking the web material with fiduciary marks longitudinally therealong.

FIG. 9B is a diagrammatic top perspective view of the web material containing fiduciary marks.

BEST MODE OF CARRYING OUT THE INVENTION

Figure 1:
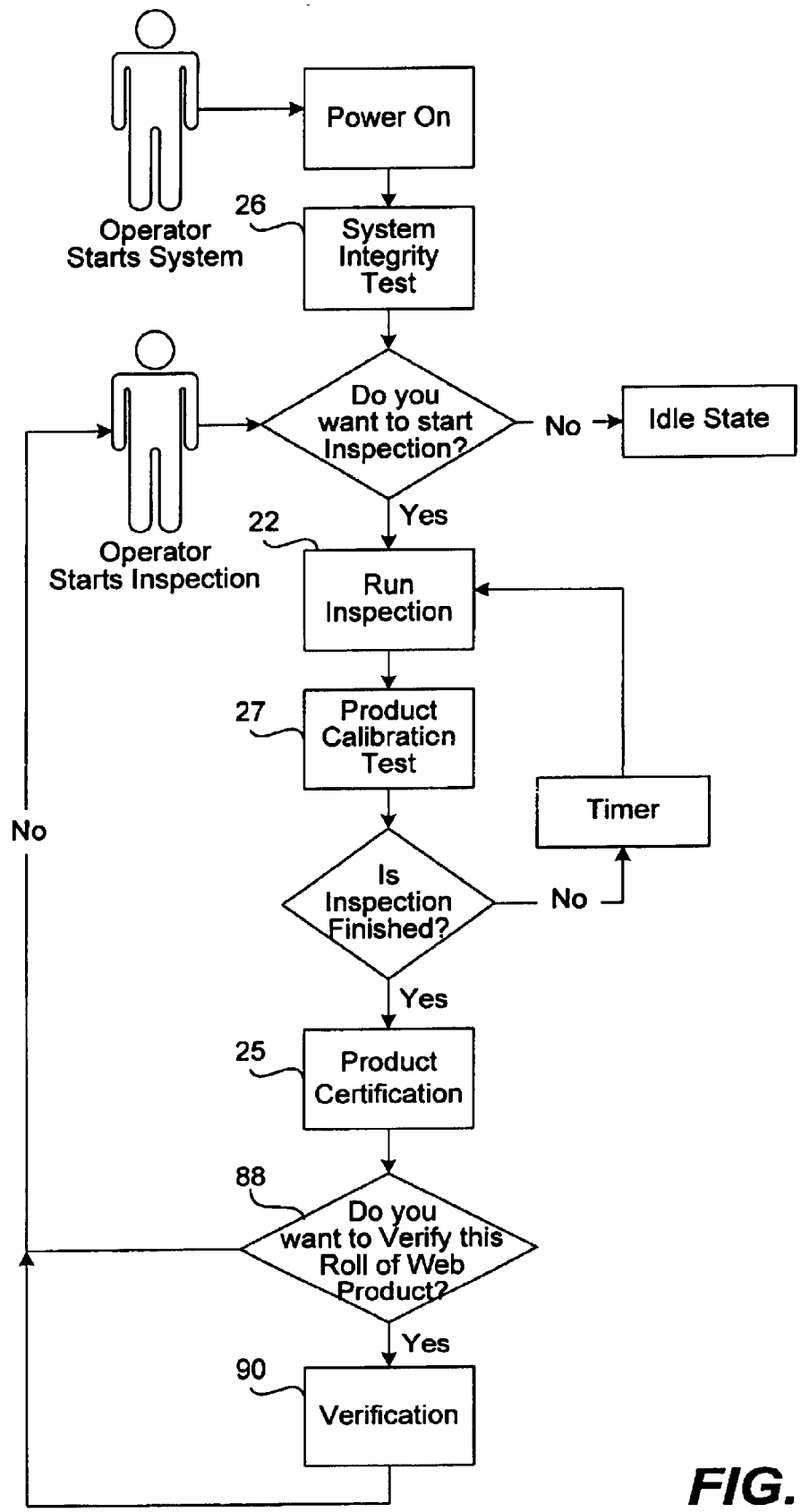
FIG. 1 is a flow diagram of the system overview of the Certification Management System (CMS) constructed in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 2:
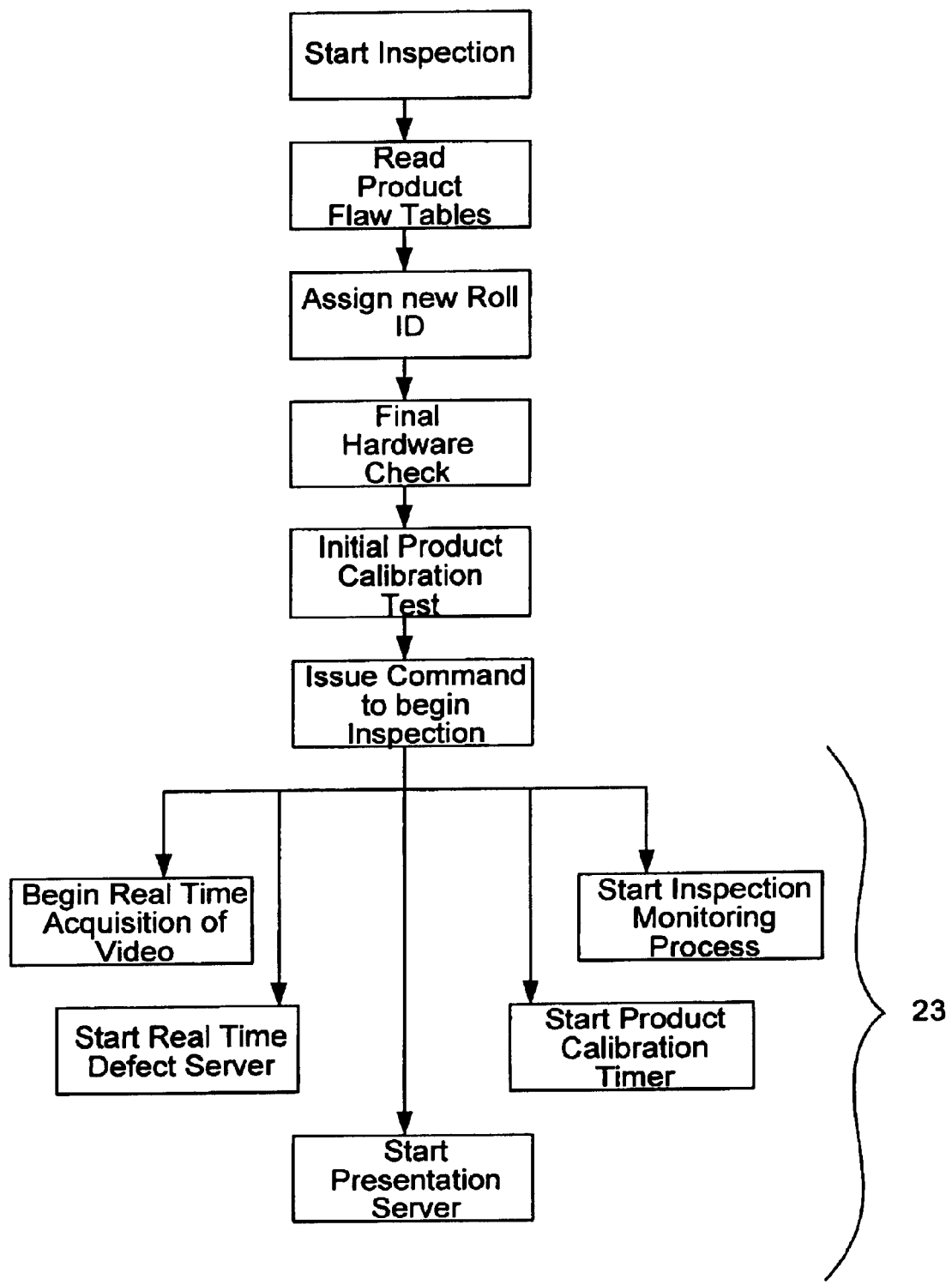
FIG. 2 is a flow diagram illustrating a web inspection of a roll of web material by a web inspection system incorporated into the CMS of the present invention.
Figure 4:
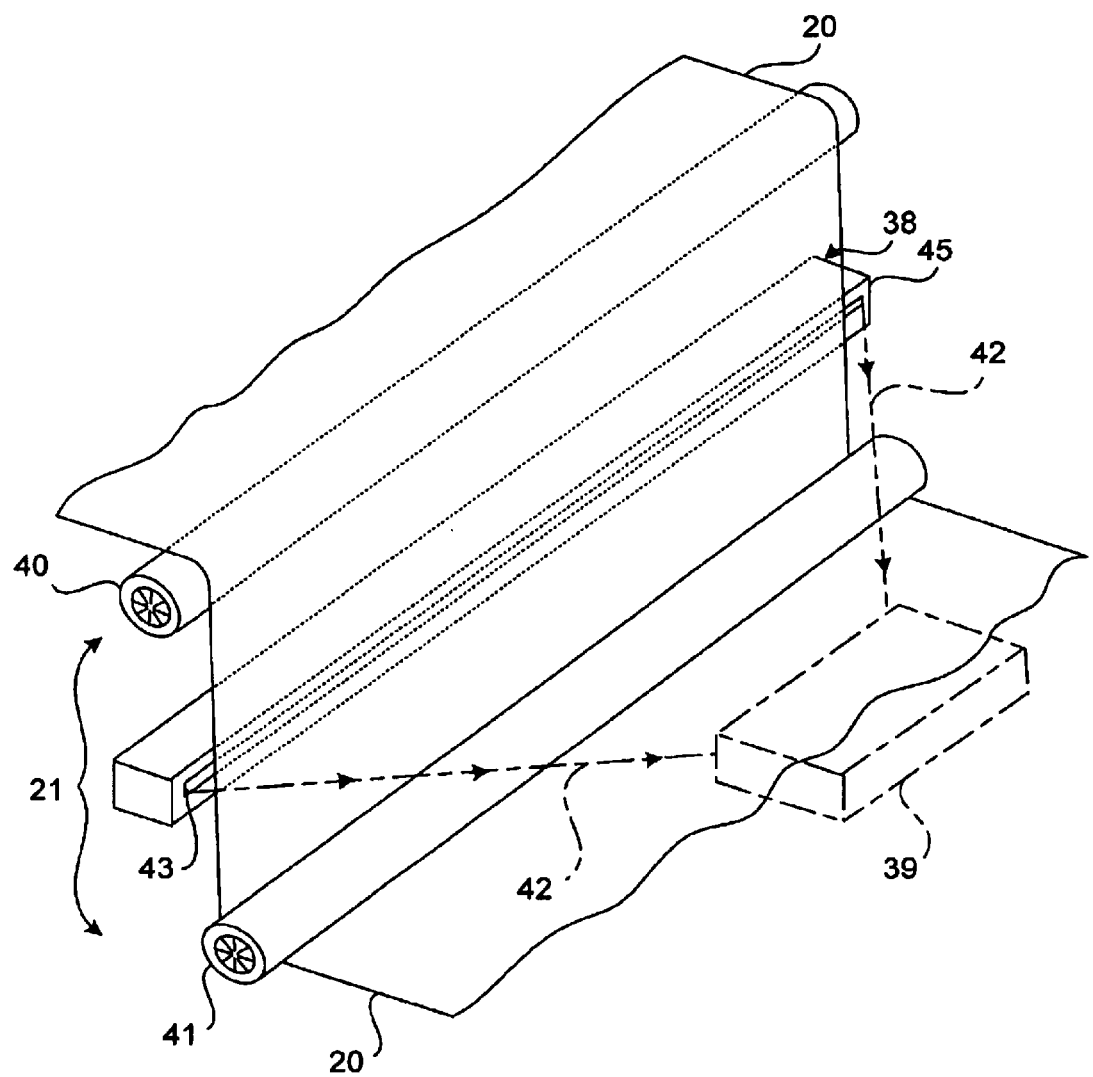
FIG. 4 is a top perspective view of a web inspection system for inspection of the material web employed by the CMS of the present invention.

Attention is now directed to FIGS. 1, 2 and 4 where a method is provided for inspection of a roll of web material 20 through a web inspection system 21 (FIG. 4). The method, briefly, includes inspecting the roll of web material 20 at 22 to determine the number, type and location of one or more detectable defects 24 (FIGS. 10A and 10B) along the web material. The method further includes outputting a data "object" representation of the roll map at 23 (FIG. 2); and certifying the accuracy of the roll map object representation of the inspected web material 20 to be within a predetermined range of tolerances, at 25 (FIG. 1).

Accordingly, such "certification" assures with a substantial degree of accuracy that the machine vision hardware (i.e., the web inspection system 21) is calibrated and operating correctly both before and during the inspection process. This signifies, as will be discussed, that a self-diagnosis has been performed done within a specified time, and the signals from the cameras are consistent with correct operation of the system. The "Product Inspection Certificate" further assures that the correct system setup parameters for the particular web product being inspected are being used. The customer's engineering staff typically sets up these parameters to achieve the desired level of defect detection, on a product-by-product basis. The Product Inspection Certificate specifies which set of parameters were used, and that they have not been altered. Finally, another main objective of the Product Inspection Certificate is to assure that the flaw report and roll map are what the system generated, and not a fabrication.

Moreover, the present invention optionally provides verification of the initial inspection through re-inspection of the roll of web material, either in the same or reverse direction. This operation will verify number, type and location of the detected defects of the initial inspection should the outcome of the reinspection substantially match the original inspection. Re-inspection will facilitate calibration of the roll map and the certification report to possible fiduciary marks, or the actual flaw distribution. This will enable the roll map object to be accurately aligned with the actual roll, and allow known flaws to be culled with confidence so that they may be identified and removed from the web material with substantial precision. The material may stretch or shrink slightly, and this process allows this to be adjusted for. Further, any new flaws are known to have been introduced by handling and shipping. Accurate damage claims are possible, as well as remediation of handling and shipping procedures.

Briefly, certification of the roll map object representation is preferably performed through self diagnostic tests which are to be triggered periodically, manually or during every run. These diagnostic tests review certification data relating to the inspection which, as mentioned, include vision hardware calibration data and operation data and product set-up calibration parameters of the web material being inspected. Thus, as viewed in FIGS. 1, 5 and 6, the analysis of the certification data is preferably divided into a System Integrity Test at 26 and a Product Calibration Test at 27. As will be described in greater detail below, the System Integrity Test relates to the operating performance of the predetermined machine vision hardware components. For example, to determine whether the cameras are aligned, focused and functioning properly. The Product Calibration Test, in contrast, relates to the calibration of the machine vision hardware for the particular type web material being inspected. For instance, depending upon the thickness and type of material inspected, the threshold settings would require input such as brightness values used to determine if a flaw is in view of a camera. A flaw may be brighter or darker than the background web material, for example, or it may have some other attribute, such as roughness, that a camera can detect.

Figure 3:
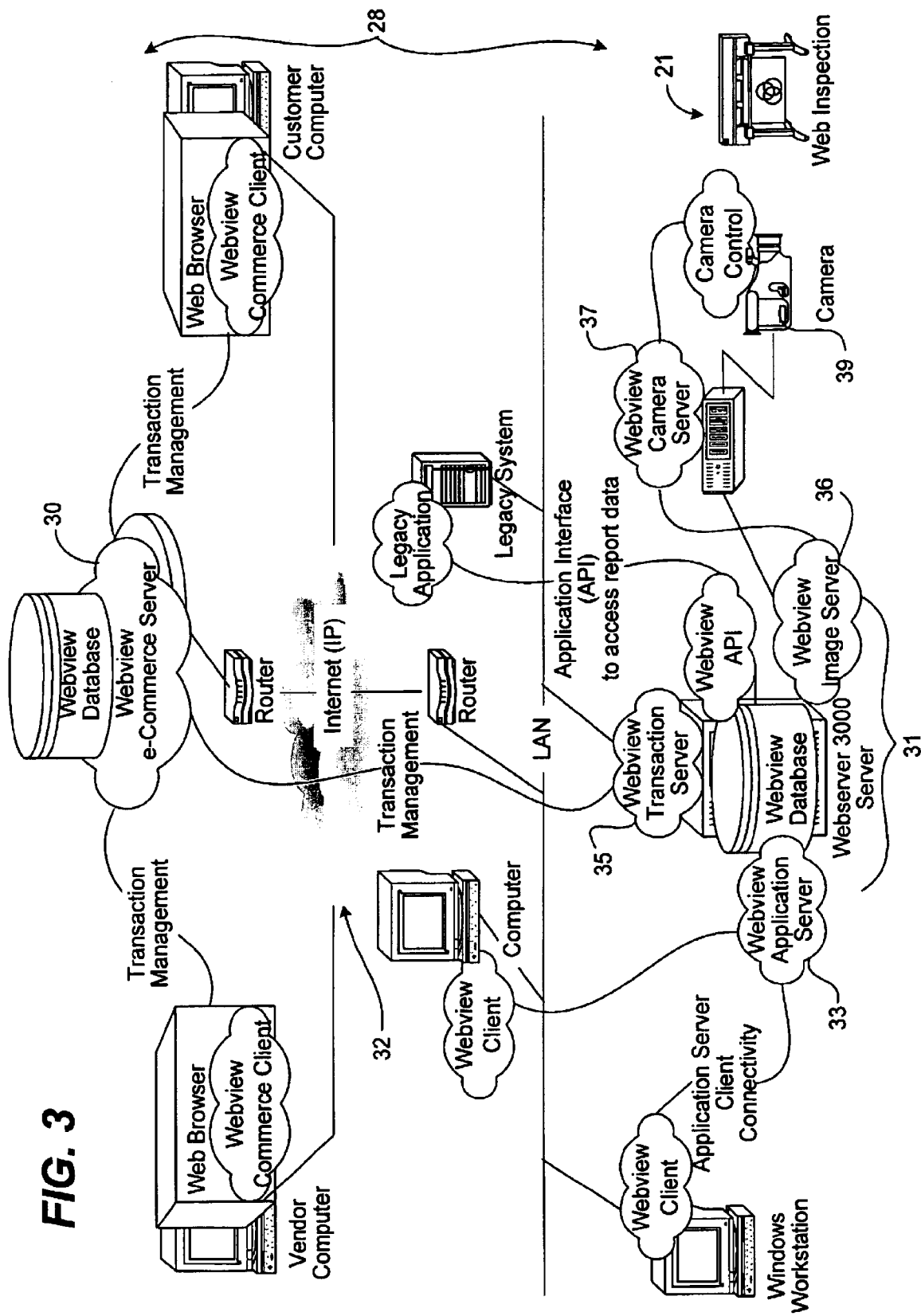
FIG. 3 is a schematic representation of the Certification Management System (CMS) incorporated into an Internet application.

The certification method of the present invention is primarily performed through the application of a Certification Management System (CMS), generally designated 28 (FIG. 3), to certify the inspection of a roll of web material 20. The CMS 28 either includes or cooperates with web inspection system 21 which is adapted to inspect the roll of web material 20 to detect at least one or more defects, if any, in the web material 20 (FIGS. 2–4). Preferably, as will be described in greater detail, the CMS 28 includes a central Commerce Server 30 which interacts with multiple Remote Servers 31 and web inspection systems 21. Hence, the central Commerce Server 30 functions as a controller enabling the distributed processing of web inspection data.

The CMS is preferably constructed around a client-server architecture, which greatly enhances flexibility and overall system customization. The present invention can be configured to be controlled through a browser interface, so that it can potentially be operated from any authorized work station connected the Internet. By designing the user interface of present invention inspection system to be browser-based, as web pages, virtually any computer can be used for monitoring of the inspection process. Moreover, while the present invention is preferably designed for application using the Internet, any network design may be applied.

Briefly, as best viewed in FIG. 3, the CMS 28 preferably includes a central Commerce Server 30 in communication with Remote Servers 31 via the Internet 32. The Remote Server 31 is preferably located at the site of the web inspection system 21, but may, of course, be situated off-site as well. As will be discussed in greater detail below, the Remote Server 31 at each inspection site preferably includes an Application Server 33, a Transaction Server 35 and an Image Server 36 which is coupled to the Camera Server 37 of the web inspection system 21.

While this browser based interface generally simplifies management of the inspection system, it also enables many completely new capabilities and uses of the inspection data. In particular, managers and engineers can monitor their factories' yield (% of good material) in real time, from their own computers or workstations, which allows them to implement real time marketing strategies and process optimization. Moreover, partial user interfaces can be built with this technique, that will allow individuals to monitor the inspection process, without actually controlling it, through their own browser on their own workstation. Examples would be alarm conditions, quality information, etc.

Further, by implementing a major portion of the user interface (GUI) in JAVA®, much of the processing is off-loaded from the central computers to the users' PCs. This also allows other processes to simulate user actions (starting and stopping inspection, specifying roll IDs, etc), greatly increasing flexibility.

The present invention CMS is also designed on a Relational Database Model using a database that supports Structured Query Language (SQL) open standards. Unlike conventional proprietary "flat file" databases applied in most web inspection systems which make it difficult to extract the information for use by any other application, the SQL databases applied in the present invention are largely interoperable between different implementations and vendors. Many high-level business tools are built around this standard. Therefore, the present invention web inspection system will be generally compatible with many third-party tools for custom reports, and data sharing and export. This greatly enhances the utility of the data. The enhanced usability of the data makes possible novel applications, in particular the portable "certification" of roll quality, which then enables the application of the electronic Roll Map or database for subsequent downstream procedures.

Moreover, these relational databases enable selective reporting of the web inspection without providing other proprietary information which may be included in conventional proprietary "flat-files". Thus, the certification documents may be created to only contain the information relevant to the customer's process. Other proprietary Information used only to manage the manufacturer's process are not needed, and may be inappropriate to distribute to the final consumer. For instance, the web inspection system may be extremely sensitive and may detect many anomalies on the material web that are in fact not flaws, but just part of the material. These are traditionally known as "Go defects", and can be excluded from the final reports provided as part of roll certification. Such selective reporting can be controlled by the engineer as part of the product setup.

Referring now to FIG. 4, a relatively conventional web inspection and web inspection system 21 will be described for a better understanding of the present invention. The inspection system 21 includes a light source or illumination system 38 operably mounted proximate the camera 39. It will be appreciated, however, that multiple cameras can be used. The sheet of material web 20 is shown being advanced longitudinally along spaced rollers 40 and 41. A bright, uniformly distributed, collective, line of light 42 is emitted from an elongated slit 43 provided in housing assembly 45 of illumination system 38. In this arrangement, the material web is inspected through backlighting where the collective line of illumination 42 is transmitted transversely through the material, as opposed to a reflected light inspection assembly employed for more opaque material webs. It will be appreciated, however, that in the latter arrangement, the illumination system 38 would be positioned on the same side of the material web 20 as camera 39, and angled with respect to the material web to reflect light into the camera lens.

In either illumination configuration, the inspection is performed using a conventional linear Charge Coupled Device (CCD) array or linescan camera 39 and proprietary hardware and software. Camera exposures are triggered by counts of the tachometer encoder, ensuring a predetermined number of scans per inch of web movement. Each scan is digitized and analyzed for defects, which are detected by changes in the linescan properties. Linescans containing defects are compared against other linescans to build up complete pictures of defective material.

Defects, once detected, are then classified using predetermined product parameters such as width, length, area, aspect ratio, relative brightness or darkness, location on the web, proximity to other defects, and mode of detection which are provided by Product Flaw Tables, to be described below. Briefly, these tables are provided by the customer, and further may be downloaded from the central Commerce Server 30. Images of defects are provided in real-time, along with location details and alarms, if desired. All inspection parameters and defects located are stored in the local database of the Remote Server 31 for later usage.

One defect detection technique employed is to compare the digitized line scan to pre-determined defect "thresholds", i.e., voltage values which any portion of a line scan may not exceed. If any portion of a line scan violates any active defect threshold, a defect classification process is started. Further linescans are examined to determine if contiguous defects are seen. If so, the line scans are merged to produce "whole" defects. It will be appreciated, however, that other defect techniques may be employed.

Briefly, the web inspection system 21 of the present invention creates visual images by first sending the camera signal (here still in analog form) through amplification and filtering devices which reduce camera noise and create specific channels of video which may be used for enhanced detection and visualization of defects. Depending on the inspection parameters, one of these channels is saved for visualization purposes. One example of such visualization techniques is disclosed in our U.S. patent application Ser. No. 09/012,342, filed Jan. 23, 1998, now U.S. Pat. No. 6,236,429, entitled "VISUALIZATION SYSTEM AND METHOD FOR A WEB INSPECTION ASSEMBLY", and incorporated by reference in its entirety.

Flaws, as compared to defects, are processed by line scan to discover contiguous flaw areas which cross linescans. This is used to "build-up" flaws until a complete flaw has been detected. Once this occurs, flaws are passed to the flaw processing code which compares flaw information with information stored in the database for flaw characterization. Flaws, once classified, are presented to the system operator in image form, along with identification of the flaw location and type on a roll-map object or graphical representation.

It is precisely this flaw type and location information accordingly, that the Certificate Management System of the present invention primarily certifies for accuracy, and that the web inspection had been performed properly. Thus, referring back to FIG. 1, once the web inspection run of FIG. 2, the System Integrity Test and the Produce Calibration Test are satisfactorily completed, the Certification Management System (CMS) certifies the roll map information at 25. Preferably, the CMS generates a hardcopy or a digital "Product Inspection Certificate" which provides a portable "certification" of roll quality that may be easily accessed for current use, or in further downstream (to be described in greater detail in the flow diagram of FIG. 8). In the preferred embodiment, this Product Inspection Certificate is a jointly generated document or report which is created by the above-mentioned web inspection system and the customer, in that the web inspection system provides the data for the System Integrity Test, while the customer provides the product data applied in the Product Calibration Test.

The method and application of the Certificate Management System will now be described in greater detail. As previously-indicated, the self diagnostic test of the predetermined certification data (relating to the performance of the machine vision hardware, and the input parameters of the web material product) is primarily divided into two independently performed tests (i.e., the System Integrity Test and the Product Calibration Test). The System Integrity Test, for instance, is performed on predetermined components of the web inspection system 21 (such as the machine vision hardware) to determined if the web inspection system is properly calibrated and is operating correctly. For example, the Integrity Test may diagnose whether the inspection cameras and light sources are correctly aligned and focused, or whether the signals generated by the cameras are consistent with correct operation protocols. Further, when the system is operating correctly, there will be certain signal levels from the sensors—light levels seen by the cameras, a valid tachometer signal, etc. These parameters are not a guarantee that the system is working at 100% reliability, but will improve the probability that a number of gross failures have not occurred, such as lighting failure, cable disconnects, etc.

The System Integrity Test will generate a time-stamped report, and create a degree of confidence, depending on how recently it was done. Each system or sub-system will have a recommended self-test interval. If the most recent self-test was performed prior to this interval, this will be cited in the certificate as an exception. The responsible engineer can still issue the certificate, but the system will note this exception. The date stamps are maintained in the system's database.

It will be appreciated, of course, that field technicians or the like must initially conduct a conventional calibration of the components, especially the precision vision hardware instruments. Typically, the initial calibration is performed manually and complies with the minimum calibration requirements specified as a system wide standard. Camera alignment, focus, and light source alignment need to be periodically adjusted and calibrated.

Figure 5:
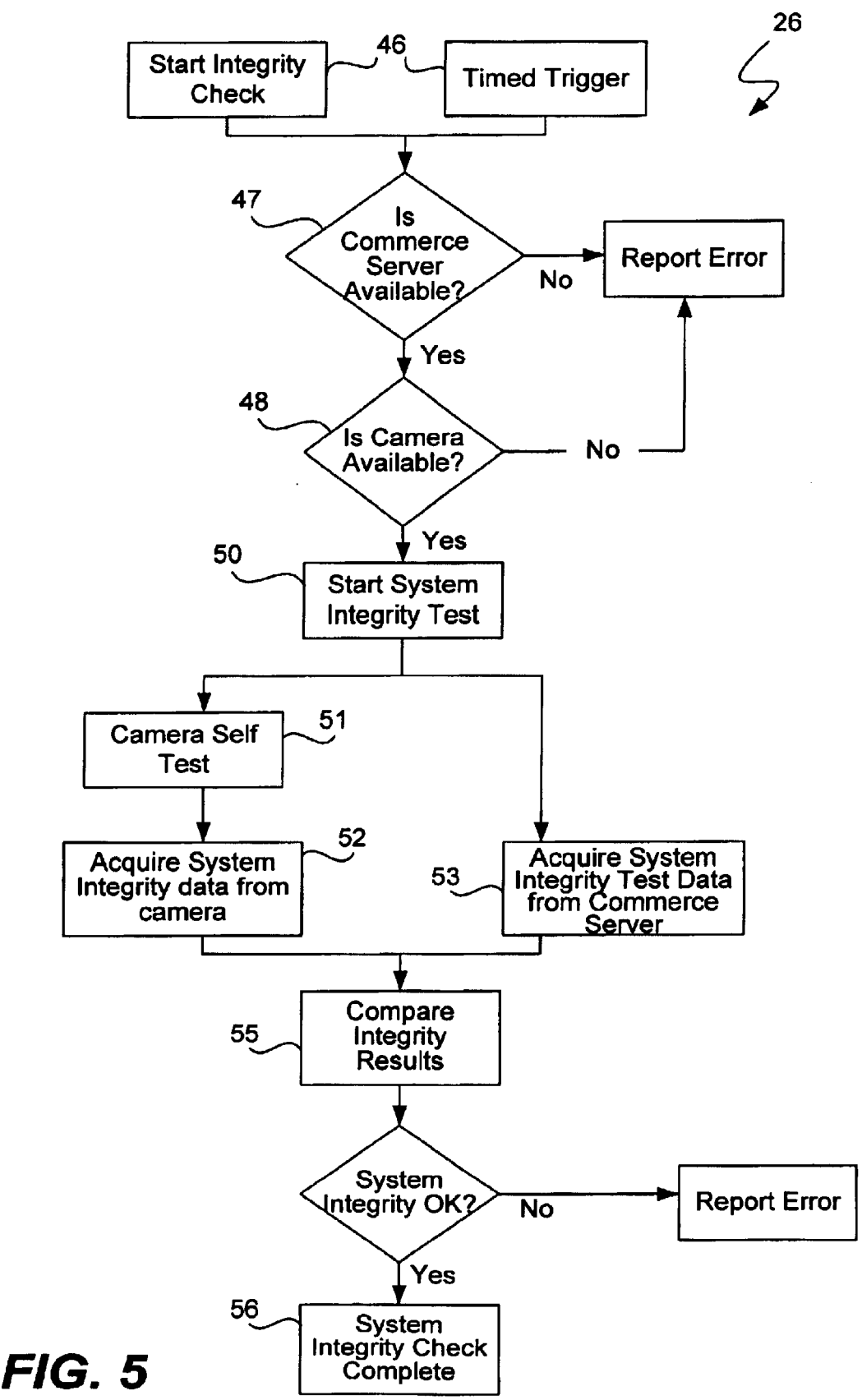
FIG. 5 is a flow diagram of the System Integrity Test illustrating the steps involved to test the system components of the web inspection system.

Referring now to FIG. 5, the System Integrity Test (26 of FIG. 1) commences at 46 which may either be manually triggered, timed trigger or automatically trigger at any time (preferably the beginning) of each inspection run. The Application Server 32 of the Remote Server 31 (FIG. 3) establishes a connection, via the Internet 32, with the Commerce Server 30 at 47 to request system availability. Next, at 48, the CMS 28 requests availability of camera 39 of the machine vision hardware of the web inspection system 21. Should these queries be satisfied, the Application Server 32 commences the actual components diagnostic test at 50. The Application Server 32 commands the camera server 37 to begin the self diagnostic test at 51 which is performed in the camera firmware. The self measured camera or vision hardware integrity data is acquired at 52.

While the vision hardware self-test is being performed, the Application Server 32 requests and downloads the System Integrity Test Data corresponding to the particular vision hardware set-up of that web inspection system from the Commerce Server 30 at 53. Accordingly, this standard calibration data may vary from system to system, depending upon the type and number of cameras, lenses, light sources, etc, but are generally fixed installation parameters for the system. Moreover, while this integrity data may be stored locally in the Remote Server, such information is preferably stored in the central Commerce Server 30 for redundancy, and in the event of data contamination.

Such standard Integrity Data is generally in the form of database tables providing the fixed installation parameters required for that vision hardware set up. These fixed installation parameters do not change from run to run, or between products. Typically, such database tables include the number of cameras; the system configuration (e.g., how the cameras are grouped); the camera parameters (e.g., how many pixels each camera contains, type of camera, timing data for each kind of camera); the geometry of how the cameras are aimed; the tables of roller sizes on the customer's web processing equipment; and tachometer encoder information which is applied to determine the speed and footage.

In accordance with the present invention, the Application Server 32 acquires the compares (using conventional comparator means) these two data sets, (i.e., the measured System Integrity Data of the inspection system vs. the standardized System Integrity Test Data) at 55 to determine whether the measured integrity data are within a predetermined tolerance of the corresponding standardized integrity data. For example, such tolerances for tachometer pulse periodicity may include allowances for "jitter".

The System Integrity Test is then complete at 56 in FIG. 5 prior to the web inspection run commencement at 22 in FIG. 1. It will be appreciated, however, that the Integrity Test may be performed after the inspection run as well without departing from the true aspect and nature of the present invention. Similarly, while the Product Calibration Test is preferably performed after the Inspection Run at 22, this Calibration Test may also be run at any time.

Figure 6:
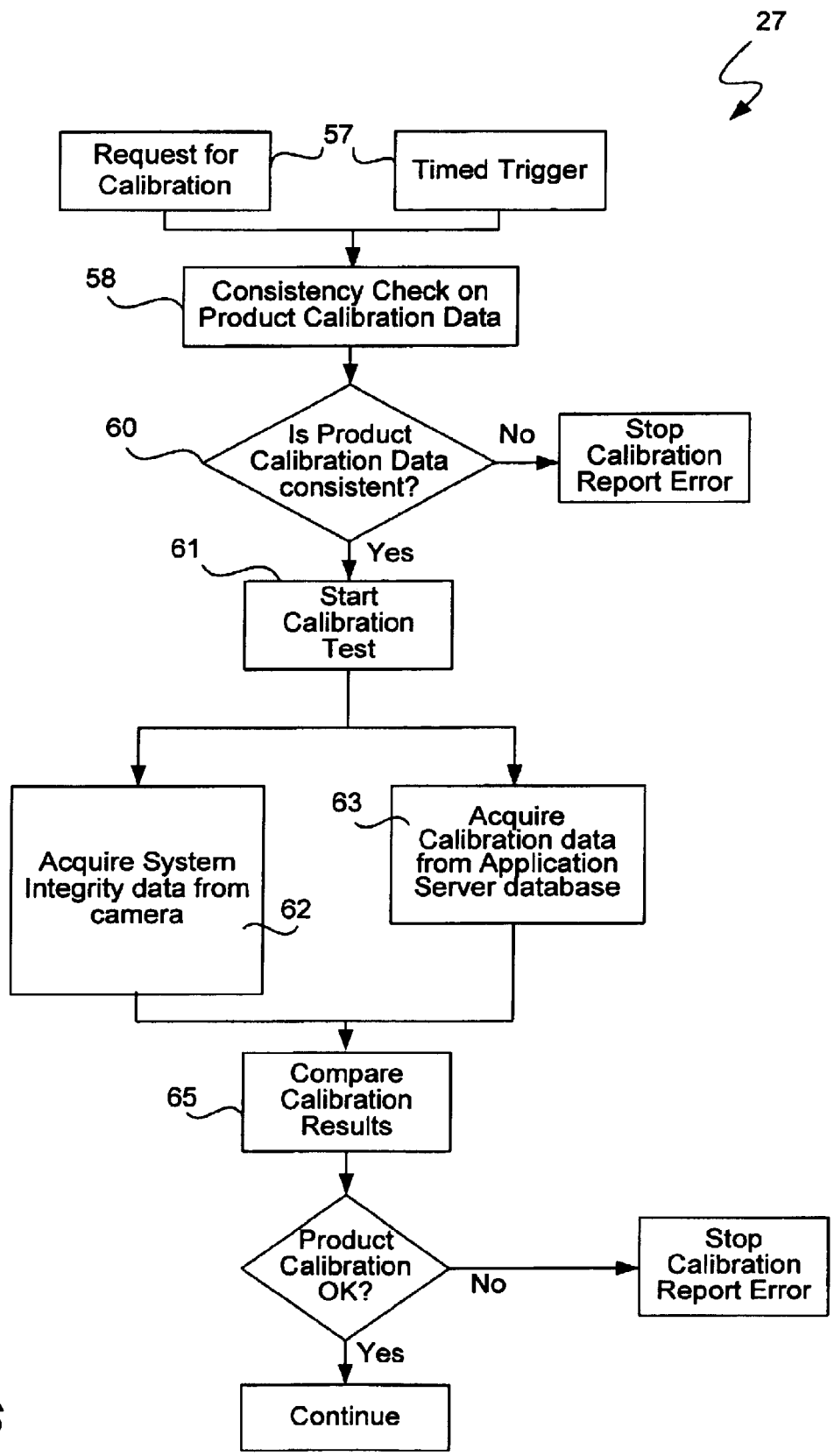
FIG. 6 is a flow diagram of the Product Calibration Test illustrating the steps involved to test the set-up parameters applied for the particular web material being inspected.

Referring now to the flow diagram of FIG. 6, the Product Calibration Test (27 in FIG. 1) is described in detail. This Calibration Test commences at 57, and again can be again be triggered manually, periodically or during each inspection run. As shown, the Application Server 32 of the Remote Server 31 retrieves the standardized Product Calibration Data for that web material 20 inspected from the Commerce Server 30 and compares this information with that locally stored in the Remote Server 31 at 58. This initial comparison is essentially a consistency or redundancy test to assure the Product Calibration Data has not been contaminated or the like.

These inspection parameters vary with the type of material inspected, and are typically provided by the customer's engineering staff. Hence, the customer sets up, provides and potentially inputs these inspection parameters to achieve the desired level of flaw detection, on a product-by-product basis.

Once the consistency of the data is satisfied at 60, the Application Server 32 commences the actual Product Calibration diagnostic test at 61. The Application Server 32 commands the camera server 37 to provide the applied Product Calibration Data which was utilized in Inspection Run for the particular web material 20. While the applied Calibration Data is being retrieved at 62, the Application Server 32 retrieves the standardized Product Calibration Data which passed the consistency test at 63.

These database tables for Product Calibration, as compared to those for the System Integrity, are per-product parameters. This product information, thus, is required to setup the inspection process and changes for different kinds of web materials that might be run. Such information may include the product names and codes, the camera settings for that web product (e.g., the exposure timing, for each camera or group of similar cameras); and threshold settings (e.g., the brightness values used to determine if a flaw is in view of a camera since a flaw may be brighter or darker than the background web material, or it may have some other attribute, such as roughness, that a camera can detect). Other set up parameters include the camera timing information for this particular product; the inspection "zones" (i.e., what part of the cameras' view is to be inspected for flaws, and conversely, what part is not of interest); and information to determine the classification of the detected flaws. This latter information, however, may be contained in separate tables, with a reference from the product tables.

At 65, the Application Server 32 of the present invention compares these two data sets, (i.e., the applied Product Calibration Data vs. the standardized Product Calibration Data for that web material) to determine whether the applied Product Calibration Data are within a predetermined tolerance of the corresponding standardized Calibration D. Examples of such tolerances include normal, minor changes in material opacity which may require changes to exposure times,.

Briefly, additional database tables include summary data applied across multiple runs and other ancillary information. These may include Run Tables which provide the other necessary information about each run, including information about flaws detected, possibly video images of flaws, etc. Examples of these tables include Run ID, Roll ID, possibly comments about the run; Time and date of the start and/or end of the run; Operator IDs—who is responsible for the run; Length of the run; and Product and Flaw table data used for this run. Since this data may be changed after the run is collected, the data from the tables at the time of the run needs to be saved with the run. Other information contained in the Run Table include Detailed information about each flaw detected; Information about problems with the run— where system overloads or failures occurred, if any; and Visualization information, if applicable. The latter may include portions of the video scans where the flaws were detected, or the entire video scans, or possible other image storage formats, such as JPEG. Other process data may be included in the Run Tables, such as readings of temperature at various points in the process, the exact location of web edges, beta gage readings of web thickness, etc. This data can sometimes be used to correlate process conditions to web quality, and provide clues to process improvement. Finally, these tables may include user IDs and passwords, user groups and access permissions, logs of system activity and parameter changes, etc. Similar to the System Integrity Data and the Product Calibration Data, this information can be certified by applying the same technique.

Referring back to FIG. 1, once the Product Calilbration Test and/or the System Integrity Test be completed (only one test may be run or required), the CMS 28 continues to the Product Certification Process at 25 of FIG. 1. This process is detailed in the flow diagram of FIG. 7, which commences at 66. At 67, the Application Server 32 reviews the flaw and defect data, generated during the inspection run (22), and the Product Calibration Data to query whether the Production Data was consistent through production of the roll. This information provides that standardized inspection methods were used throughout the entire product run to be certified.

If the Production data is consistent at 68, the process proceeds to 70 to Certify the Product Roll. This command is performed by the Application Server 32. Subsequently, at 71, the CMS 28 issues an electronic Certification Document which includes an encrypted Digital Product Inspection Certificate. The Application Server 32 of the Remote Server 31 then communicates with the Commerce Server 30 at 72 to complete the certificate transaction. This process is mission critical, and is described in greater detail below in the flow diagram of FIG. 8.

Finally, the electronic Certification Document with the Digital Certificate can be printed at 73 to provide a hard copy thereof. This document is preferably includes a coded mark, and is attached to the roll of web material.

In another aspect of the present invention, the CMS 28 enables safe transaction of the Inspection Certificate via the Internet 32 (FIG. 3) to all authorized users of the system. This ensures that the Inspection Certificate is logged on the local Application Server 32 and then transferred to the Commerce Server 30 which is acting as the "Host" in the CMS 28.

Each Application Server 32 will be capable of making secure transactions with the Commerce Server 30. The transaction will be fail safe so that data integrity will be maintained at all times. The transacted Inspection Certificate will contain all necessary Inspection data pertaining to an actual inspected Product Roll.

Figure 8:
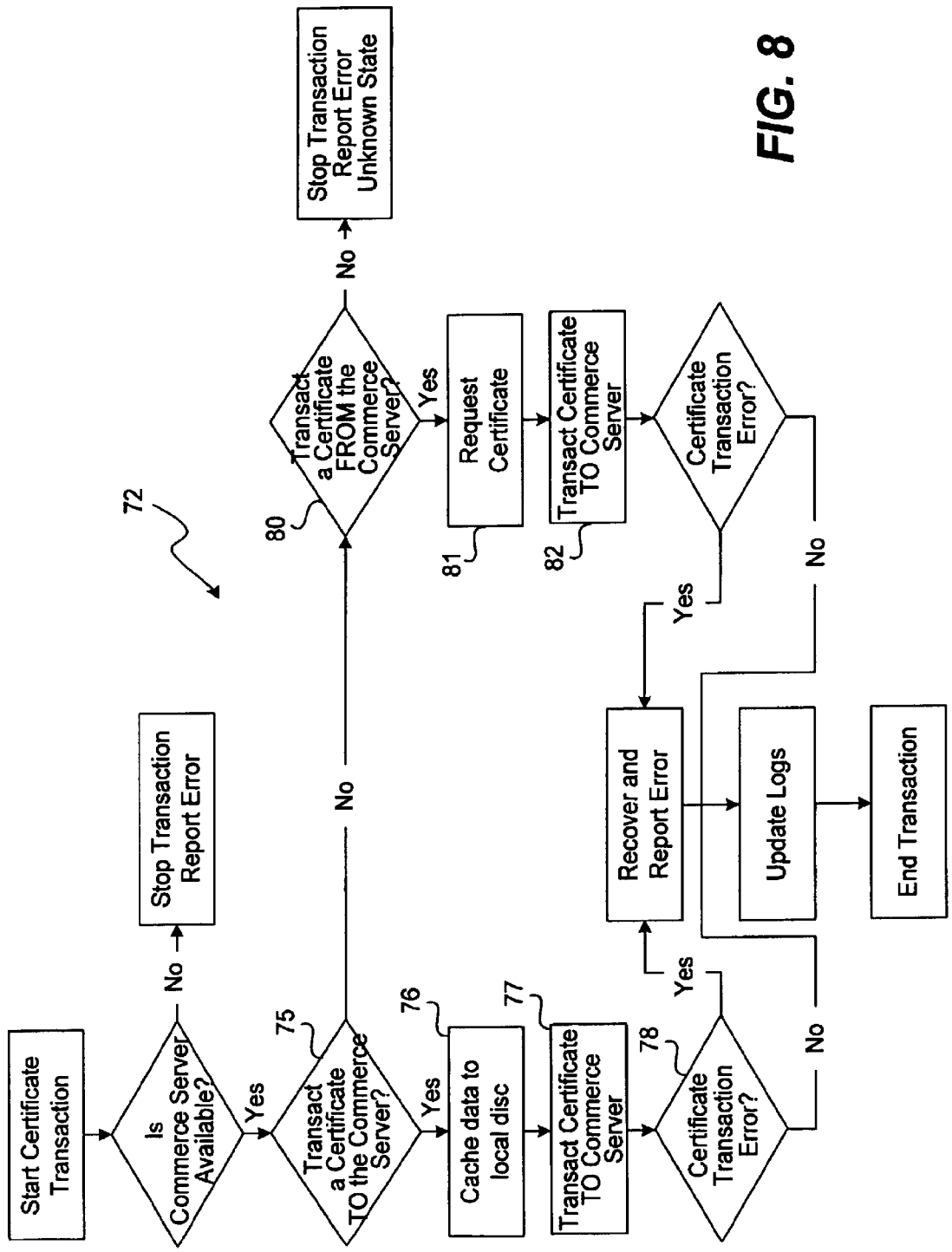
FIG. 8 is a flow diagram of the Certification Transaction Process depicting a simple transaction model to transfer an electronic product inspection "certificate" between an inspection system client and the Commerce Server.

Accordingly, as shown in the Certificate Transaction Process of FIG. 8, The Application Server 32 of the Remote Server 31 (FIG. 3) establishes a connection, via the Internet 32, with the Commerce Server 30, at 75, to request system availability. When this is established, the Application Server queries whether to transact the data of the Inspection Certificate to the Commerce Server or not, at 76.

In the event this transaction is to occur, the Application Server 32 then writes or caches the data of the Product Inspection Certificate to the local storage medium thereof, at 77. This redundancy ensure recoverability in the event of data contamination. At 78, Application Server and the Transaction Server 35 then upload the Product Inspection Certificate to the Commerce Server 30. This guarantees safe storage and distribution to other users of the system. Moreover, a user creating the Inspection Certificate and the Roll of Web Product can publish the Inspection Certificate to the CMS System and the Certificate can then be made available to other users of the system.

Figure 11:
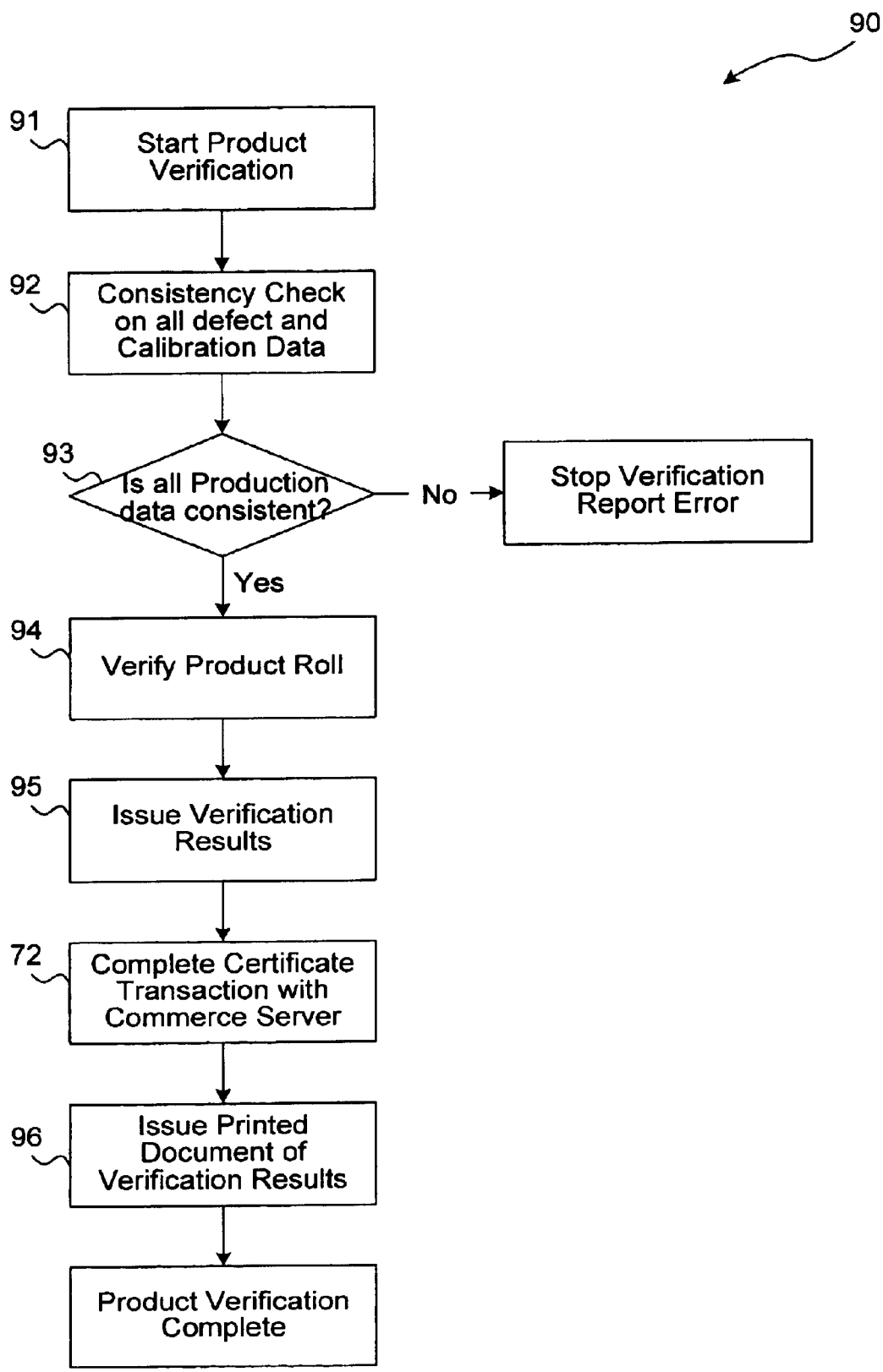
FIG. 11 is a flow diagram of the Verification Test illustrating the steps involved to verify the locational accuracy of defects detected during the web inspection.

This is illustrated, at 80 of the Certificate Transaction Process, where a Product Inspection Certificate can be requested at 81 from the Commerce Server 30. Upon authorization, the requested Certificate will be downloaded from the Commerce Server to the designated Application Server 32, at 82, for use, such as to provide a comparison data set for the downstream Verification Process of FIG. 11 (to be discussed in detail below).

Thus, as mentioned, anyone authorized to perform downstream applications of the roll of web material can retrieve the data contained in the Inspection Certificate from the central Commerce Server 30. For instance, an authorized user can download an Inspection Certificate from the CMS 28 when they take delivery of a Roll that was manufactured elsewhere and use the extrapolated data to Verify the Product Roll during Re-Inspection. In another example, a user can check Inspection Certificates online and assess product quality prior to ordering/purchasing Web Roll Products.

In another aspect, the CMS of the present invention enables verification of Product Inspection Certificate by allowing accurate re-inspection of the original inspection. This is advantageous in several respects. For example, one obvious purpose is to simply recertify the web material 20 and verify the Product Inspection Certificate. Accordingly, any new flaws or changes to the material since the original inspection, perhaps introduced by handling and shipping, will be revealed. Thus, more accurate damage claims are possible, as well as remediation of handling and shipping procedures.

Moreover, the actual footage of the web material can be verified with accuracy. Applying fiduciary indicators (to be discussed below) along the web material, the inspection system 21 can adjust for normal stretching or shrinkage of the web material between manufacture and use, or with different web tensions. Accordingly, shortages or missing section of the material from the web can be detected since the time of original inspection and certification.

In accordance with this aspect of the present invention and as illustrated in FIG. 9B, fiduciary indicators 85 are established on the material web 20. Preferably, these indicators are in the form of fiduciary marks 86 placed longitudinally along the roll. These marks 86 may be introduced during manufacture or during the original inspection of the web material in a manner that doesn't damage the useable material. One non-intrusive location may be along one longitudinal edge of the roll. Preferably, these marks can be provided by ink, adhesive flags, or hole punches in non-useable edges of the material.

Upon re-inspection, these marks 86 can again be detected, as a means of recalibration of the location of the defects or flaws. Accordingly, unlike the current web inspection designs, when electronic Roll Maps of the web roll are recorded during prior inspections of the web material, the CMS 28 of the present invention enables proper synchronization along the web surface to effectively and precisely outline the flaw types and their locations, during further downstream applications at the same or different manufacturing systems. Thus, the roll map will be accurately aligned with the actual roll, and the location of the reported defects can be accurately verified. With the precision calibration that is possible using this technique, the known flaws or defects can be culled with confidence. Consequently, the current practice of rejecting the entire lot (i. e., web roll), due to defects which cannot be accurately located, can be eliminated.

Figure 10A:
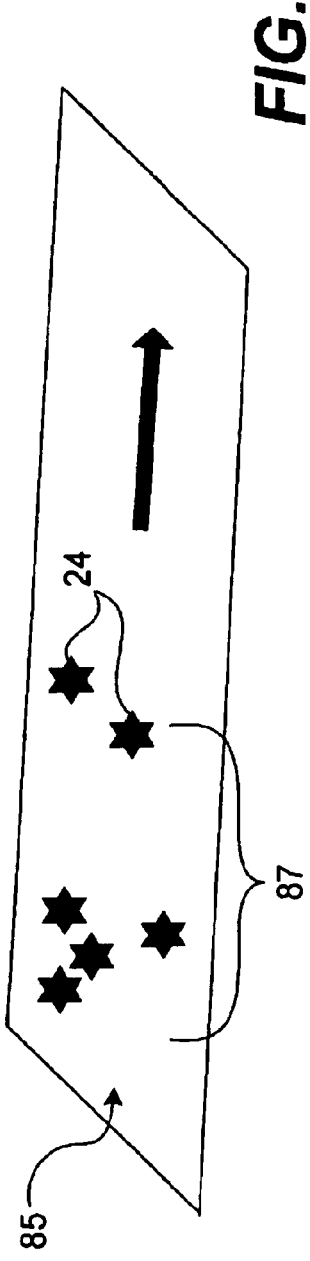
FIG. 10A is a diagrammatic top perspective view of the web material containing a defect or flaw pattern being utilized as fiduciary indicators longitudinally therealong.
Figure 10B:
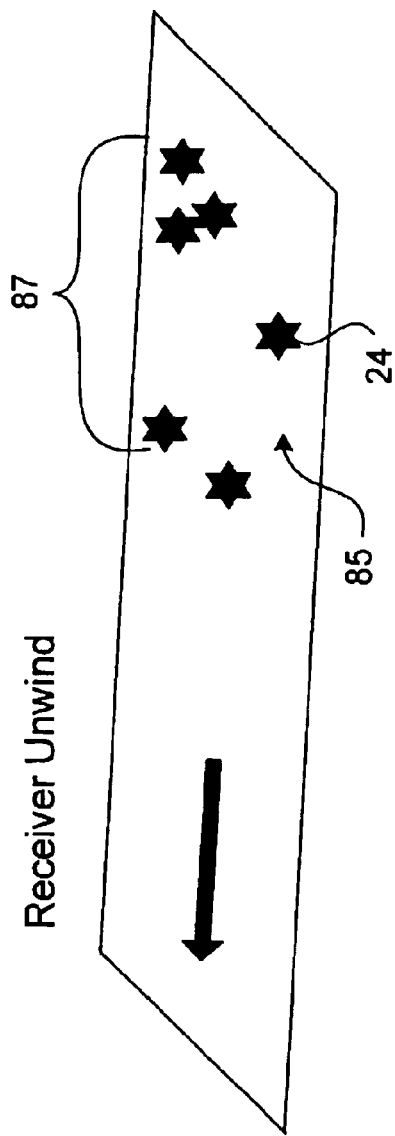
FIG. 10B is a diagrammatic top perspective view of the web material being re-inspected in the reverse direction for recalibration of the defect or flaw pattern of fiduciary indicators.

Referring now to FIGS. 10A and 10B, the flaw distribution or pattern 87 of defects themselves can function as fiduciary indicators 85 longitudinally along the roll of the web material. Upon the real-time recognition of the pattern or distribution of flaws by the CMS 28 during the re-inspection, their location thereof along the web can be verified. When the number of flaws or the distribution is too sparse, fiduciary marks will be required.

Whether fiduciary mark or the flaw distribution or pattern are employed as fiduciary indicators, the re-inspection may be performed in either direction (FIGS. 10A and 10B). This is advantageous in that the re-inspection will not require that the roll of web material be rewound so that it will be re-inspected in the same "windup" direction of the original manufacture. This is primarily performed by software which will transpose the coordinates to compensate for the "last is now first" order of flaws and marks.

Accordingly, referring back to FIG. 1, at 88 the CMS 28 queries whether to commence the optional Product Verification Process at 90. Upon commencement, the Verification Process starts at 91 of FIG. 11.

Figure 7:
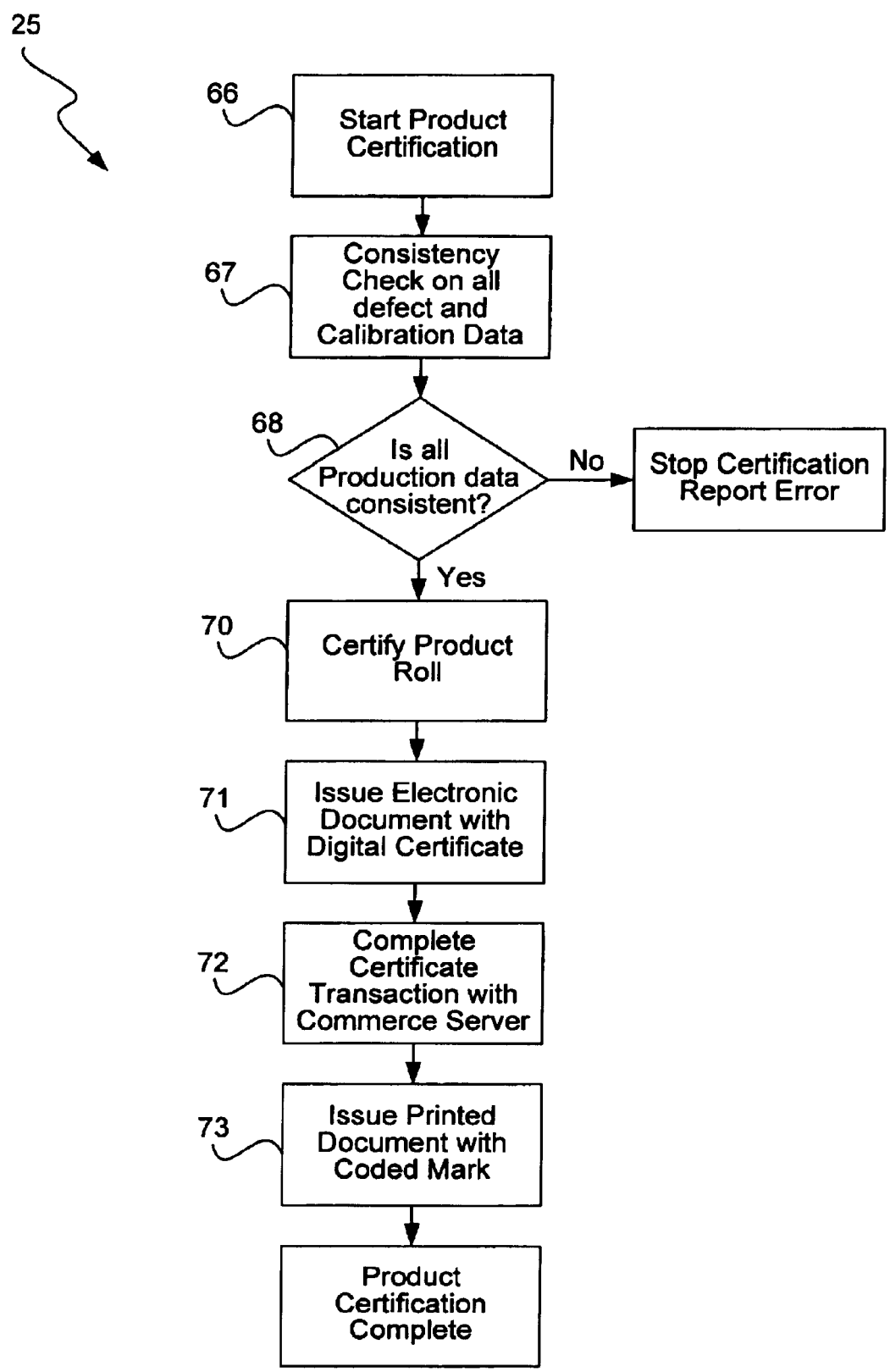
FIG. 7 is a flow diagram describing the Product Certification Process, where the Inspection has been completed and the CNIS checks whether the data acquired during the inspection is consistent and issues the Inspection Certificate.

Initially, at 92, the Application Server 32 reviews the flaw and defect data and the Product Calibration Data to query whether the Production Data was consistent through production of the roll (similar to 67 in the Product Certification Process of FIG. 7). This information again ensures that standardized inspection methods were used throughout the entire product run to be certified.

If the Production data is deemed consistent at 93, the process proceeds to 94 to Verify the Product Roll. In this verification, the Application Server 32 downloads the original "Product Inspection Certificate" from the central Commerce Server 30, and compares the detected number, pattern, distribution and/or type of defect or flaw during the re-inspection with the original roll map to verify the consistency of the results. Any changes, relative the original roll map, will be recorded, and cited in the verification report.

Subsequently, at 95 the CMS 28 issues an electronic Certification Document which includes an encrypted Digital Product Inspection Certificate. The Application Server 32 of the Remote Server 31 then communicates with the Commerce Server 30 at 72 to complete the certificate transaction. As mentioned, this process is mission critical, and is described in greater detail in the flow diagram of FIG. 8.

Finally, the electronic Certification Document with the Digital Product Inspection Certificate can be printed at 96 to provide a hard copy thereof. This document is preferably includes a coded mark, and is attached to the roll of web material.

The "Product Inspection Certificate", being a digital document, is preferably digitally signed to guarantee authenticity. Thus, the CMS 28 of the present invention enables the application of digital signatures to be created and attached to the entire input document. Any other system can verify the signature, which is encrypted in such a way that only the creator could have made it. It is a "strong" guarantee of authenticity—it is known that forging a digital signature is extremely difficult, or practically impossible.

Further, these digitally signed documents can be filed, over the Internet, with public services that track and time-stamp the signatures for legal verification at a later time, should the need arise. The verification of this signature is part of the Product Inspection Certificate. Accordingly, if an operator or the like has altered the setup to achieve an incorrectly "good" quality, the signature on the setup will not check out, and the exception will be noted. In fact, all operator interactions with the system can be audited to the log file. Thus if a question comes up, an investigation will show any peculiarities.

In addition to the Product Inspection Certificate, any appropriate reports generated by the system, which are pre-defined as part of the setup, may include an associated digital signature for them. Since the setup is also certified, it is clear if the required reports are missing or altered since the time stamps won't match, signifying that the reports are not genuine.

The Certificate Management System 28 will optionally generate an Invoice (Bill of Material) that explicitly states the quality of the material and the exact location of all defects. This document will also be provided with a digital signature when it is created.

Although the foregoing invention has been described in some detail for purposes of clarity of understanding, it will be apparent that certain changes and modifications may be practiced within the scope of the appended claims.

What is claimed is:

1. A method for inspection of a roll of web material through a web inspection system comprising:

inspecting a roll of web material to determine a number, type and location of one or more detectable defects along the web material;

outputting an electronic data representation of a roll map, including real-time visual images of the one or more detectable defects;

storing the electronic data representation to enable subsequent retrieval thereof;

performing a Self-Diagnostic Test on said web inspection system to determine the performance of the web inspection by the web inspection system, including:

measuring or retrieving actual certification data applied during said inspection; and comparing the actual certification data to standardized certification data to determine whether the actual certification data was within a predetermined range of tolerances;

performing a System Integrity Test measuring performance and calibration of predetermined components of the web inspection system; and certifying an accuracy of the roll map electronic data representation of the inspected web material to be within a predetermined range of tolerances set for that web material.

2. The method according to claim 1 wherein, said performing a Self-Diagnostic test further includes performing a Product Calibration Test measuring or reviewing an application of product set-up parameters for the particular web material inspected.

3. The method according to claim 1 wherein, said actual certification data includes System Integrity Test Data relating to a calibration and operation of predetermined components of the web inspection system, and Product Calibration Test Data reviewing product set-up parameters applied for the particular web material inspected.

4. The method according to claim 1 wherein, said certifying includes generating a digital Product Inspection Certificate containing and certifying the data representation of the roll map.

5. The method according to claim 4, wherein said certifying further includes generating a digital signature with the Product Inspection Certificate.

6. A method for certifying an inspection of a roll of web material through a web inspection system comprising:

calibrating the web inspection system to conform to predetermined certification data for the roll of web material to be inspected;

inspecting the roll of a web material for one or more defects, if any, through the web inspection system;

detecting at least one of the one or more defects through the web inspection system, including real-time visual images of the at least one or more detectable defects;

determining a location of the at least one detected defect, relative the roll of web material, through fiduciary indicators placed along the web material;

recording the detection of the at least one or more detected defects, their real-time visual images thereof, and their location relative the roll of web material on an electronic recording medium to create an electronic roll map;

measuring actual certification data of the web inspection system;

comparing the actual certification data to the predetermined certification data for the roll of web material;

certifying an accuracy of the roll map of the inspected web material when the actual certification data is within a predetermined tolerance of the predetermined certification data; and re-inspecting the roll of web material through the same web inspection system or an independent second web inspection system to verify the certification by detecting the at least one of the one or more defects, through the web inspection system.

7. The method according to claim 6 wherein, said actual certification data includes System Integrity Test Data of predetermined components of the web inspection system, and said measuring includes performing a self diagnostic test on said predetermined components to generate the actual certification data.

8. The method according to claim 7 wherein, said performing a Self-Diagnostic Test is performed periodically within a predetermined time interval.

9. The method according to claim 8, further including:
time stamping the performance of the Self-Diagnostic Test.

10. The method according to claim 7 wherein, said performing a Self-Diagnostic Test is performed before each web inspection run.

11. The method according to claim 7 wherein, said predetermined components include vision hardware of the web inspection system.

12. The method according to claim 11 wherein, said vision hardware includes at least one of a camera, a lens and a light source.

13. The method according to claim 12 wherein, said System Integrity Test Data includes at least one of camera alignment, lens focus and light source alignment.

14. The method according to claim 6 wherein, said actual certification data further includes Product Calibration Data corresponding to the particular web material being inspected, and said measuring includes determining what inspection set-up parameters were employed during the web inspection, and determining that the inspection set-up parameters have not been altered.

15. The method according to claim 14 wherein, said system inspection set-up parameters include a desired level of flaw detection.

16. The method according to claim 14 further including:
providing said inspection set-up parameters by a customer.

17. The method according to claim 6, further including:
time stamping a current measuring of the actual certification data.

18. The method according to claim 6, wherein said certifying includes generating a Product Inspection Certificate including the actual certification data, the predetermined certification data, and the roll map.

19. The method according to claim 6, wherein said certifying further includes generating a digital signature with a certification report.

20. The method according to claim 6, further including:
determining a cause of the at least one detected defect.

21. The method according to claim 20, wherein said determining the cause includes comparing measured defect data of the at least one detected defect with existing defect data of a process-control database.

22. The method according to claim 6, wherein said re-inspecting the roll further includes:
determining the location of the at least one detected defect, relative the roll of web material, through fiduciary indicators placed along the web material;

recording the detection of the at least one detected defect, and its location relative the roll of web material on a recording medium to create a roll map;

measuring actual certification data of the web inspection system;

comparing the measured actual certification data to the predetermined certification data for the roll of web material; and recertifying the accuracy of the second roll map of the inspected web material when the secondly measured actual certification data is within the predetermined tolerance of the predetermined certification data.

23. The method according to claim 22, wherein said fiduciary indicators are provided by placing fiduciary marks along said roll of web material.

24. The method according to claim 23, wherein said placing fiduciary marks is performed during the first indicated inspection of said roll of web material.

25. The method according to claim 24, wherein said fiduciary marks are placed along an edge of the web material.

26. The method according to claim 6, wherein said re-inspection is performed on the roll of web material in an opposite direction of the first indicated web inspection.

27. The method according to claim 6, further including: verifying a location of the at least one or more defects by comparing a determined location, relative to the roll of web material and relative to the fiduciary indicators to the placed along the web material during the first inspection, of the at least one detected defect to the determined location, relative to the roll of web material and relative to the fiduciary indicators to be placed during the re-inspection thereof, of the at least one detected defect.

28. The method according to claim 6, further including: determining said fiduciary indicators by the detection of the at least one or more defects along said roll of web material.

29. A web inspection certification system to certify an inspection a roll of web material through a web inspection system comprising:
   a web inspection system adapted to inspect a roll of web material applying certification data relating to the web inspection system and the particular web material to detect at least one or more defects, if any, therein, their type, their location relative the web material, and their real-time visual image thereof, said inspection system generating an electronic data representation of a roll map;
   a recording device configured to record the electronic data representation for subsequent retrieval thereof;
   a diagnostic device adapted to measure or retrieve actual certification data of the web inspection system applied or to be applied during said web inspection corresponding to the particular web material being inspected;
   a certifying device adapted to certify an accuracy of the electronic data representation of the roll map of the inspected web material when the actual certification data conforms, within a predetermined tolerance, to standardized certification data for the roll of web material; and
   a time stamp device to time stamp the occurrence of a Self-Diagnostic Test performed by the diagnostic device.

30. The system according to claim 29 wherein, said actual certification data includes System Integrity Test Data of predetermined components of the web inspection system.

31. The system according to claim 30 wherein, said predetermined components include vision hardware of the web inspection system.

32. The system according to claim 31 wherein, said vision hardware includes at least one of a camera, a lens and a light source.

33. The system according to claim 32 wherein, said System Integrity Test Data includes at least one of camera alignment, lens focus and light source alignment.

34. The system according to claim 30 wherein, said actual certification data further includes Product Calibration Data corresponding to the particular web material being inspected to certify which product set-up parameters were employed during the web inspection, and that the product set-up parameters have not been altered.

35. The system according to claim 34 wherein, said product set-up parameters include a desired level of flaw detection.

36. The system according to claim 29, wherein said certifying device is configured to generate a Product Inspection Certificate including the actual certification data, predetermined certification data, and the roll map.

37. The system according to claim 36, wherein said certifying device is further adapted to generate a digital signature with the Product Inspection Certificate.

38. The system according to claim 29, further including: a defect analysis device configured to determine a cause of a detected defect by comparing measured defect data of the at least one detected defect with existing defect data of a process-control database.

39. The system according to claim 29, further including: a location analysis device configured to determine a location of the at least one detected defect, relative the roll of web material, through fiduciary indicators placed along the web material.

40. The system according to claim 39, wherein said fiduciary indicators include spaced-apart fiduciary marks placed along said roll of web material.

41. The system according to claim 40, wherein said fiduciary marks are spaced-apart along an edge of the web material.

42. The system according to claim 39, wherein: said fiduciary indicators include the detected one or more defects relative their placement along said roll of web material.

43. A method for inspection of a roll of web material through a web inspection system comprising:
   inspecting a roll of web material to determine a number, type and location of one or more detectable defects along the web material;
   outputting an electronic data representation of the roll map, including real-time visual images of the one or more detectable defects;
   storing the electronic data representation to enable subsequent retrieval thereof;
   performing a Self-Diagnostic Test on said inspection system to determine the performance of the web inspection by the inspection system, including:
      measuring or retrieving actual certification data applied during said inspection; and
      comparing the actual certification data to standardized certification data to determine whether the actual certification data was within a predetermined range of tolerances, said actual certification data includes System Integrity Test Data relating to the calibration and operation of predetermined components of the web inspection system, and Product Calibration Test Data reviewing product set-up parameters applied for the particular web material inspected; and
   certifying an accuracy of the roll map electronic data representation of the inspected web material to be within a predetermined range of tolerances set for that web material.

44. The method according to claim 43 wherein,
said certifying includes generating a digital Product Inspection Certificate containing and certifying the data representation of the roll map.

45. A method for certifying an inspection of a roll of web material through a web inspection system comprising:
calibrating the web inspection system to conform to predetermined certification data for the roll of web material to be inspected;
inspecting the roll of a web material for one or more defects, if any, through the web inspection system;
detecting at least one of the one or more defects through the web inspection system, including real-time visual images of the at least one or more detectable defects;
determining a location of the at least one detected defect, relative the roll of web material, through fiduciary indicators placed along the web material;
recording the detection of the at least one or more detected defects, their real-time visual images thereof, and their location relative the roll of web material on an electronic recording medium to create an electronic roll map;
measuring actual certification data of the web inspection system, which includes performing a Self-Diagnostic Test on vision hardware of the web inspection system, said actual certification data includes System Integrity Test Data of said vision hardware including at least one of camera alignment of a camera, lens focus of a lens, and light source alignment of a light source;
comparing the actual certification data to the predetermined certification data for the roll of web material; and
certifying an accuracy of the roll map of the inspected web material when the actual certification data is within a predetermined tolerance of the predetermined certification data.

46. The method according to claim 45 wherein,
said performing a Self-Diagnostic Test is performed periodically within a predetermined time interval.

47. The method according to claim 45, further including:
time stamping the occurrence of the Self-Diagnostic Test.

48. A method for certifying an inspection of a roll of web material through a web inspection system comprising:
calibrating the web inspection system to conform to predetermined certification data for the roll of web material to be inspected;
inspecting the roll of a web material for one or more defects, if any, through the web inspection system;
detecting at least one of the one or more defects through the web inspection system, including real-time visual images of the at least one or more detectable defects;
determining a location of the at least one detected defect, relative the roll of web material, through fiduciary indicators placed along the web material;
recording the detection of the at least one detected defect, and its location relative the roll of web material on a recording medium to create a roll map;
recording the detection of the at least one or more detected defects, their real-time visual images thereof, and their location relative the roll of web material on an electronic recording medium to create an electronic roll map;
measuring actual certification data of the web inspection system and performing a Self-Diagnostic Test on predetermined components of the web inspection system to generate the actual certification data within a predetermined time interval;
time stamping the occurrence of the Self-Diagnostic Test;
comparing the actual certification data to the predetermined certification data for the roll of web material; and
certifying an accuracy of the roll map of the inspected web material when the actual certification data is within a predetermined tolerance of the predetermined certification data.

49. The method according to claim 48 wherein,
said actual certification data includes System Integrity Test Data of at least one of a camera, a lens and a light source of the predetermined components.

50. The method according to claim 49 wherein,
said System Integrity Test Data includes at least one of camera alignment, lens focus and light source alignment.

51. A web inspection certification system to certify an inspection a roll of web material through a web inspection system comprising:
a web inspection system adapted to inspect a roll of web material applying certification data relating to the web inspection system and the particular web material to detect at least one or more defects, if any, therein, their type, their location relative the web material, and their real-time visual image thereof, said inspection system generating an electronic data representation of a roll map;
a recording device configured to record the electronic data representation for subsequent retrieval thereof;
a diagnostic device adapted to measure or retrieve actual certification data of the web inspection system applied or to be applied during said web inspection corresponding to the particular web material being inspected, said actual certification data includes System Integrity Test Data including at least one of camera alignment of a camera, lens focus of a lens, and light source alignment of a light source of the web inspection system; and
a certifying device adapted to certify an accuracy of the electronic data representation of the roll map of the inspected web material when the actual certification data conforms, within a predetermined tolerance, to standardized certification data for the roll of web material.

52. The system according to claim 51, wherein
said certifying device is configured to generate a Product Inspection Certificate including the actual certification data, predetermined certification data, and the roll map.

53. The system according to claim 51, further including
a defect analysis device configured to determine a cause of a detected defect by comparing measured defect data of the at least one detected defect with existing defect data of a process-control database.

54. The system according to claim 51, further including
a time stamp device to time stamp the occurrence of a Self-Diagnostic Test performed by the diagnostic device.

55. A web inspection certification system to certify an inspection a roll of web material through a web inspection system comprising:
a web inspection system adapted to inspect a roll of web material applying certification data relating to the web inspection system and the particular web material to detect at least one or more defects, if any, therein, their type, their location relative the web material, and their real-time visual image thereof, said inspection system generating an electronic data representation of a roll map;

a recording device configured to record the electronic data representation for subsequent retrieval thereof;

a diagnostic device adapted to measure or retrieve actual certification data of the web inspection system applied or to be applied during said web inspection corresponding to the particular web material being inspected, said actual certification data includes System Integrity Test Data of predetermined components of the web inspection system, and Product Calibration Data corresponding to the particular web material being inspected to certify which product set-up parameters were employed during the web inspection, and that the product set-up parameters have not been altered; and a certifying device adapted to certify an accuracy of the electronic data representation of a the roll map of the inspected web material when the actual certification data conforms, within a predetermined tolerance, to standardized certification data for the roll of web material.

56. The system according to claim 55, further including a defect analysis device configured to determine a cause of a detected defect by comparing measured defect data of the at least one detected defect with existing defect data of a process-control database.

57. The system according to claim 55, further including:

a time stamp device to time stamp the occurrence of a Self-Diagnostic Test performed by the diagnostic device.

58. A web inspection certification system to certify an inspection a roll of web material through a web inspection system comprising:

a web inspection system adapted to inspect a roll of web material applying certification data relating to the web inspection system and the particular web material to detect at least one or more defects, if any, therein, their type, and their real-time visual image thereof, said inspection system generating an electronic data representation of a roll map;

a diagnostic device adapted to measure or retrieve actual certification data of the web inspection system applied or to be applied during said web inspection corresponding to the particular web material being inspected;

a certifying device adapted to certify an accuracy of the electronic data representation of the roll map of the inspected web material when the actual certification data conforms, within a predetermined tolerance, to standardized certification data for the roll of web material;

a location analysis device configured to determine a location of the at least one detected defect, relative the roll of web material, through fiduciary indicators placed along the web material; and a recording device configured to record the detection of the at least one detected defect, and its location relative the roll of web material to create the roll map thereof;

wherein said fiduciary indicators include the detected at least one or more defects themselves relative their placement along said roll of web material.

59. The system according to claim 58, further including:

a time stamp device to time stamp the occurrence of a Self-Diagnostic Test performed by the diagnostic device.

60. A method for certifying an inspection of a roll of web material through a web inspection system comprising:

inspecting the roll of a web material for one or more defects, if any, through the web inspection system;

detecting at least one of the one or more defects through the web inspection system;

determining a location of the at least one detected defect, relative the roll of web material, through fiduciary indicators placed along the web material;

recording the detection of the at least one detected defect, and its location relative the roll of web material on a recording medium to create a roll map; and re-inspecting the roll of web material through the same web inspection system or an independent second web inspection system, in an opposite direction of the first indicated web inspection, to verify a certification by detecting the at least one of the one or more defects, through the web inspection system.

* * * * *